United States Patent [19]
Lane

[11] Patent Number: 6,139,504
[45] Date of Patent: Oct. 31, 2000

[54] FILTER FOR USE IN AN ACOUSTIC IMAGING DEVICE

[75] Inventor: Charles Lane, Duxbury, Mass.

[73] Assignee: Hood Laboratories, Pembroke, Mass.

[21] Appl. No.: 09/150,221

[22] Filed: Sep. 9, 1998

Related U.S. Application Data

[63] Continuation-in-part of application No. 08/944,347, Oct. 6, 1997, Pat. No. 5,848,973.
[51] Int. Cl.$^7$ ....................................................... A61B 5/08
[52] U.S. Cl. .......................................... 600/529; 600/533
[58] Field of Search .................................... 600/437, 459, 600/529, 533, 540, 433, 462, 463, 407

[56] References Cited

U.S. PATENT DOCUMENTS

| | | | |
|---|---|---|---|
| 5,195,528 | 3/1993 | Hok | 600/529 |
| 5,666,960 | 9/1997 | Fredberg et al. | 600/529 |
| 5,823,965 | 10/1998 | Rasmussen | 600/462 |
| 5,902,237 | 5/1999 | Glass | 600/407 |

*Primary Examiner*—Marvin M. Lateef
*Assistant Examiner*—Ali M. Imam
*Attorney, Agent, or Firm*—Pitney, Hardin, Kipp & Szuch, LLP

[57] ABSTRACT

In a device for acoustic imaging of internal morphology of the respiratory tract which utilizes a hollow acoustic pipe having a speaker on one end and microphones on its side wall the improvement comprising a disposable tube or sleeve which is intended to be coextensive with the pipe, having a filter at its far end and filters to fit over the microphones along with a lip or ring at its outer end so as to avoid cross-contamination between patients whose breath enters the pipe.

14 Claims, 4 Drawing Sheets

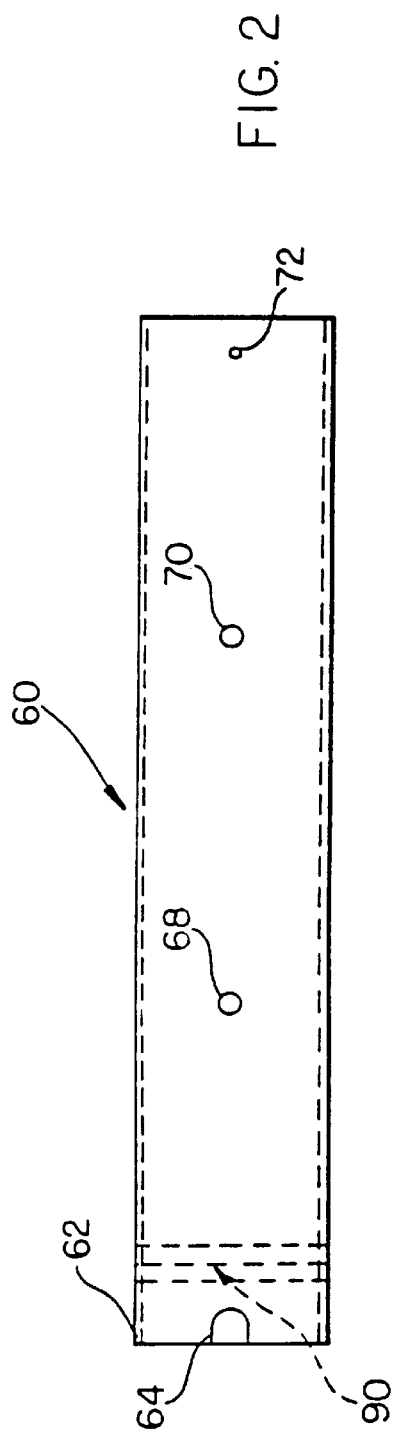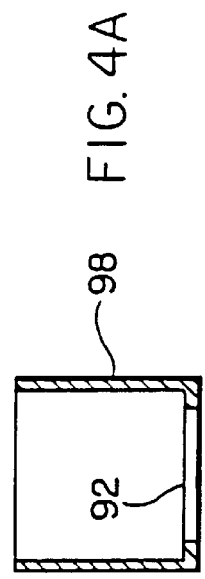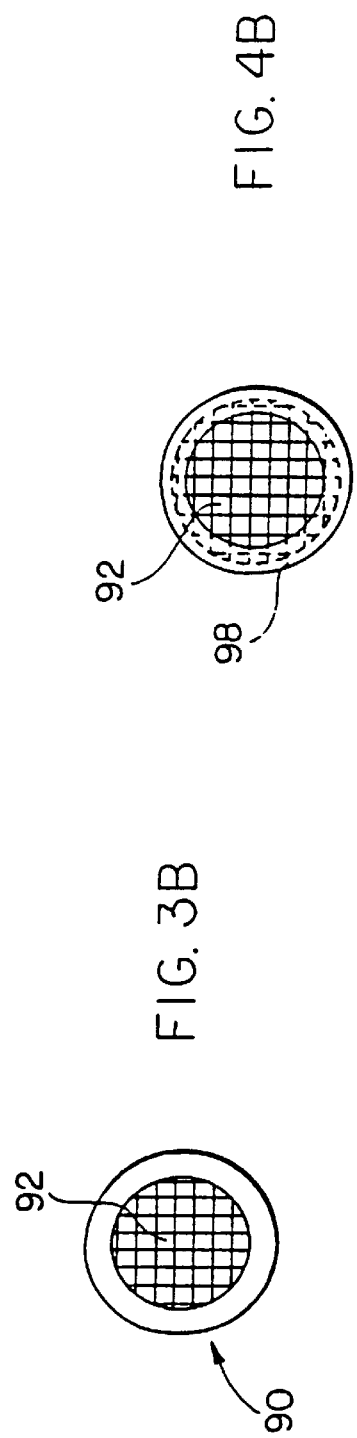

FILTER FOR USE IN AN ACOUSTIC IMAGING DEVICE

RELATED APPLICATIONS

This application is a continuation-in-part of U.S. application Ser. No. 08/944,347 filed Oct. 6, 1997 now U.S. Pat. No. 5,848,973 entitled "Filter For Use In an Acoustic Imaging Device".

FIELD OF THE INVENTION

This invention relates to a filter and sleeve for use in an acoustic imaging device which is used for imagery of mammalian airway morphology and more particularly concerns noninvasively obtaining a signal representative of the cross-sectional area of an airway (e.g., oral, nasal, or pulmonary) of a subject (e.g., a person or an animal) using electroacoustical transducers.

BACKGROUND OF THE INVENTION

The present invention is directed toward improving the acoustic imagery device as set forth in U.S. Pat. No. 5,666,960 entitled "Acoustic Imaging" which issued on Sep. 16, 1997, the disclosure of which is incorporated herein by reference. This patent is assigned to Hood Laboratories, 575 Washington Street, Pembroke, Mass. 02359 and Biomechanics, Inc., 25 Bay State Road, Boston, Mass. 02359. Hood Laboratories sells a Pharyngometic Wavetube in which the present invention can be utilized.

Briefly, the aforesaid patent discloses a light-weight, easy-to-use, hand-held acoustic imaging head. The imaging head is used by the operator to conduct the imaging procedure. The head comprises a housing having an elongated body, an inner acoustic pipe and other attendant elements and electronics. There is an aperture through the housing to provide communication between the pipe and outside the housing. During use of the device, the patient's breath may be exhaled into and inhaled from the internal pipe during, for example, pulmonary testing. Accordingly, it is desirable to prevent cross-contamination between different patients. It has become desirable to prevent this in such a way that it is simple, easy and inexpensive to do so.

SUMMARY OF THE INVENTION

It is therefore a principle object of this invention to provide for, in an acoustic imaging device herein discussed, a means of preventing cross-contamination between patients.

It is a further object of this invention to do so in a simple, easy and inexpensive manner.

It is a yet further object of this invention to provide the foregoing while not interfering with the operation of the device.

These and other objects and advantages will be apparent with the present invention which provides for a thin walled tube or sleeve for insertion into the acoustic pipe of the imaging device. Provided in the tube are hydrophobic filters which serve to protect the microphones and internal speaker from, among other things, humid exhaled air while not affecting the testing. Openings are provided and are covered with a filter material on the side of the tube and positioned so as to line up with microphones within the side wall of the acoustic pipe. The tube accordingly, does not interfere with their operation. A notch is provided in the tube to provide its proper alignment. An outer lip or ring is positioned at its open end so as to prevent contamination from entering between the sleeve and the acoustic pipe. The tube assembly is disposable so it can be discarded after use by sliding it out of the acoustic pipe. With the use of the filter tube the patient can breathe freely with cross-contamination between subjects being avoided since the tube can be discarded after use.

BRIEF DESCRIPTION OF THE DRAWINGS

Thus the present invention, its objects and advantages will be realized the description of which should be taken in conjunction with the drawings which are:

FIG. 2 is a side view of the filter tube of the present invention;

FIGS. 3A and 3B are a side and front view of the hydrophobic filter membrane of the present invention;

FIGS. 4A and 4B show an alternate means of mounting the hydrophobic filter membrane of the present invention;

DETAILED DESCRIPTION OF THE PREFERRED EMBODIMENT

Figure 1:
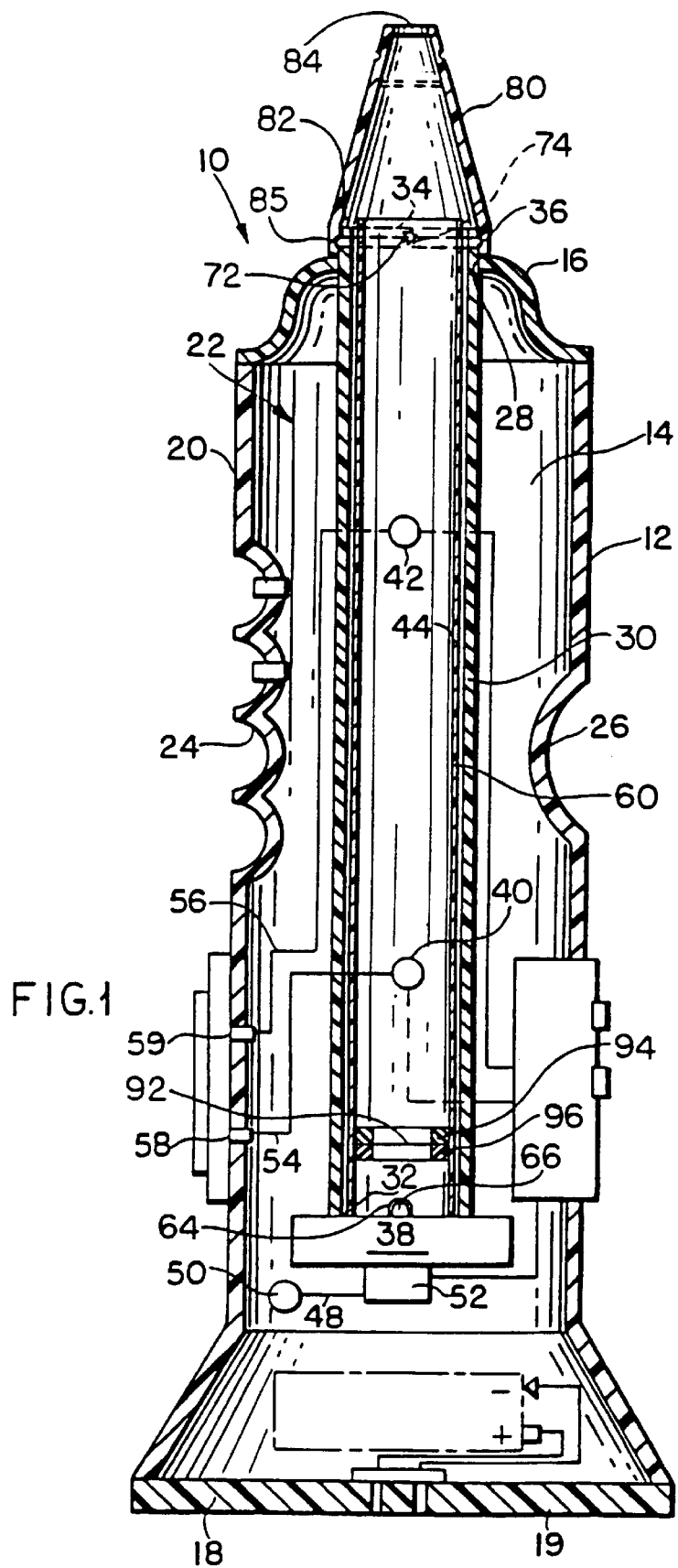
FIG. 1 is a cross-sectional side elevational view of an acoustic imaging head incorporating the filter tube of the present invention.

Turning now more particularly to the drawings, reference will be made to FIG. 1 which shows the imaging devices discussed more fully in the aforesaid patent. The device will, however, be briefly discussed. In this regard, referring to FIG. 1, a cross-sectional side elevation, there is seen a acoustic imaging head 10 for imaging the internal morphology of portions of the respiratory tract of a mammal, including a human. Head 10 comprises a hand-holdable housing 12 having an elongate body 14 defined by a top end 16 and a base end 18 which presents a planar surface 19 for standing the head 10 on a flat surface in an upright position. The housing 12 presents an outer wall 20 extending between ends 16, 18 and defining an internal, closed chamber 22. Wall 20 advantageously includes integrally molded finger holds 24 and a palm grasping indentation 26. An aperture 28 pierces end 16 of the housing 12. The aperture 28 has mounted therein end 34 of an acoustic pipe 30 having a closed first end 32 within chamber 22 and an open end 34 outside of the housing 12. The end 34 of acoustic pipe 30 includes a rib 36 encircling the circumference of end 34, which functions as a means for removably coupling to the acoustic pipe 30 an adaptor in the form of coupling device or mouthpiece 80 for mating with an orifice of the mammal respiratory tract for imaging. The acoustic pipe 30 substantially traverses chamber 22 and its dimensions dictate the overall dimensions of the housing 12. For example, the acoustic pipe 30 is advantageously about 1.0 to 4.0 cm, preferably about 1.9 cm in diameter and has a length of between about 5 to about 40 cm, most preferably 5 to 20 cm. The end 32 of pipe 30 is closed by mounting thereon a loudspeaker or launching transducer 38 which, upon energization, will launch acoustic energy into the interior of acoustic pipe 30, propagating an incident sonic wave towards open end 34 of pipe 30 and outside the end 34. When the head 10 is coupled to an orifice in the respiratory tract for imaging through coupling device 80, the propagated sound wave will enter the respiratory tract, strike anatomical features in the tract and be reflected back through end 34 into the interior of acoustic pipe 30 to form a transient wave field within the pipe 30. This wave field is representative of the morphology of the respiratory tract. Two spaced apart pressure transducers 40, 42 (such as Endevco series 8510 B microphones) are mounted on the acoustic pipe 30 with their pressure sensor flush with the inner walls of acoustic pipe 30 in order to reduce parasitic acoustic reflections. The transducers 40, 42 are advantageously separated from each other a distance of from about 1.0 to about 15 cm. and both are separated from the end 34 of acoustic pipe 30 by at least about 2.0 cm. The transducers 40, 42 are each electrically connected by separate electrical conductors 54, 56, respectively, which also can terminate in plug-type connectors 58, 59 mounted on the housing 12 wall 14. The connectors 58, 59 can be used for connection to signal processing means external of head 10.

Turning briefly to coupling device 80, it is a sterilizible, disposable nasal coupling device having an input end 82 that attaches to the output end of pipe 30 and an output end 84 for insertion into, for example, a nostril. Channel 85 on the inside wall of coupling device 80 mates with and receives the rib 36 on end 34 of tube 30, for secure, removable attachment. Channel 85 and rib 36 cooperate to provide a means for attaching the acoustic pipe 30 end 34 to the coupling device 80. Other means of attachment will be apparent to those skilled in the art, such as the so-called "bayonet mount", screws, frictional fits, male-female connectors and the like. The coupling device 80 can be made of any material suitable for purpose.

Figure 5:
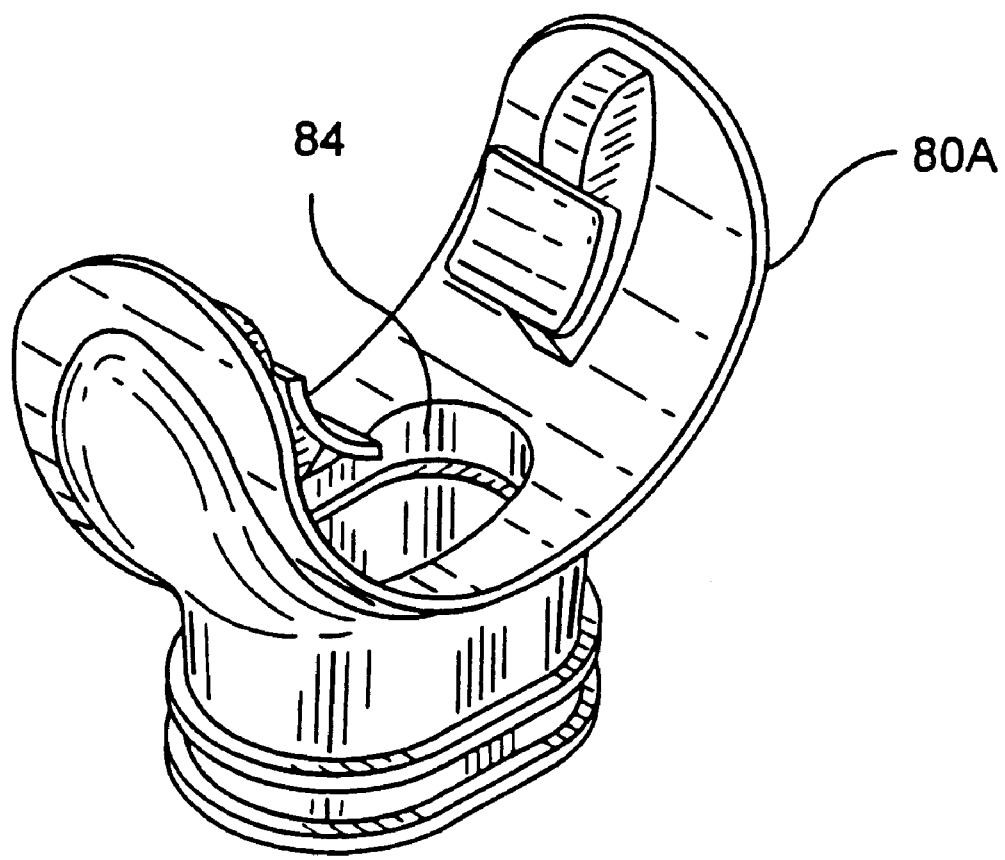
FIG. 5 shows a perspective view of an alternative coupling member to the imaging head.

Note the coupling device may also be in the form of a mouthpiece 80A as shown in FIG. 5. This has an aperture 84 and may be detachably affixed to imaging head 10 and is similar to a snorkeling mouthpiece for imaging use with the Pharyngometic Wavetube previously referred to.

Turning now to the filter tube 60, it is a hollow cylindrical tube or sleeve and preferably made out of a plastic material. It is so dimensioned that it snugly fits within the acoustic pipe 30 while being slidable therein. At its lower end 62, that being positioned adjacent end 32 of pipe 30 there is provided a notch or slot 64 which serves to match with a location post 66. When the notch 64 is in post 66 this assures that the opening 68 and 70 are properly positioned over microphones 40 and 42 so as not to interfere with their operation.

A reference dot 72 is provided and can be used in conjunction with a reference dot 74 on the outside of housing 20 in sliding the tube 60 into pipe 30. Once the tube 60 is correctly inserted, the dots 72 and 74 will be aligned with the tube 60 extending approximately ¹⁄₁₆" beyond end 34. If the tube 60 is not correctly aligned, the tube 60 will obviously extend out further since the notch 64 will not be in post 66. Rather the end of the tube 60 will be against the post 66 causing the displacement.

Within the tube 60, near end 62 is a circular hydrophobic filter 90. The filter 90 comprises a filter membrane 92 of approximately 10 microns in thickness mounted between two O-shaped bases 94 and 96 which may be made of P.V.C., A.B.S., polystyrene or any other suitable material. The filter 90 is mounted in tube 60 by way of a friction fit, adhesive or any other manner suitable for purpose and protects the speaker 38 from humid exhaled air while not affecting the acoustic testing of the patient.

In FIGS. 4A and 4B there is shown an alternative mounting of the filter. In this regard a housing 98 is provided in which the membrane 92 is squeezed down into. The housing 98 is then slid into the end 62 of the tube 60 and is maintained there in a friction fit.

After the tube 60 is placed into the pipe 30 then the coupling device 80 is placed on the housing 12. When imaging is completed, the coupling device 80 is taken off the housing 12 with tube 60 slid out and a new tube 60 slid in and device 80 replaced. The head 10 is now ready for use with a new tube whilst avoiding cross-contamination.

Figure 6:
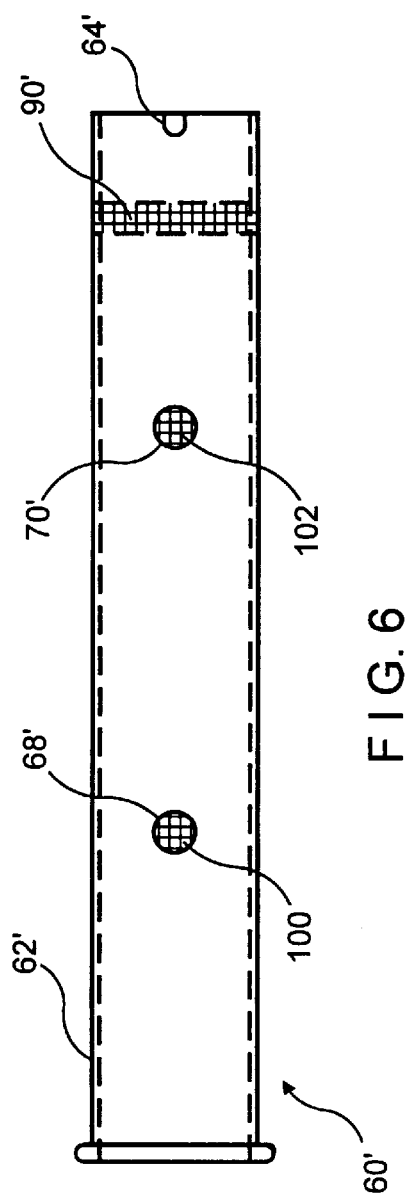
FIGS. 6 and 6A are side and longitudinal sectional views of a further embodiment of the filter tube.
Figure 6A:
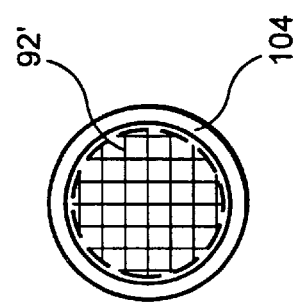
Figure 7A:
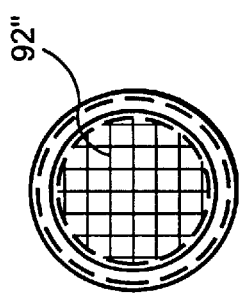

Turning now to FIGS. 6 and 6A corresponding numerical designations to the earlier embodiment are shown designated, however, with a prime. The tube 60' is provided with hydrophobic filter disks 100 and 102 positioned in or over openings 68' and 70' respectively. These disks may be glued, heat sealed or compression bonded over the openings 68' and 70'. The filter disks 100 and 102 may be made of the same hydrophobic filter material and membrane as previously described with regard to speaker filter 90.

To provide for a sealing of the space between tube 60' and acoustic pipe 30', positioned at the end of the tube 60' is an O-ring 104. This will seal the space therebetween to reduce the possibility of exhaled air from passing therethrough.

Figure 7:
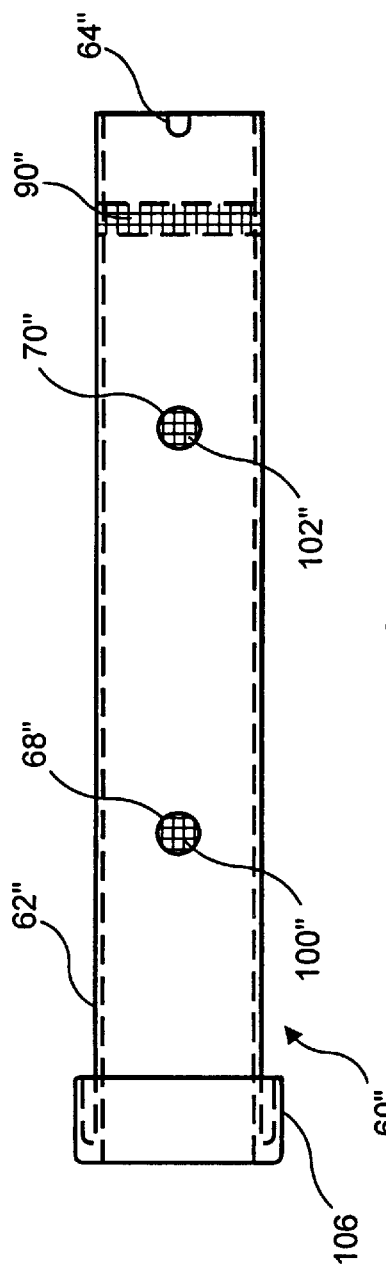
FIGS. 7 and 7A are side and longitudinal sectional views of a yet further embodiment of the filter tube.

An alternative to such a sealing method is shown in FIG. 7 where like parts are similarly numbered but designated with a double prime. In this regard, a thin, flexible, circumferential wall 106 is provided as an extension of the open end of tube 60". This wall 106, when inserted into the acoustic pipe 30" is positioned between the outside wall of pipe 30" and the inside of coupling device or mouthpiece 80.

Thus by the present invention its objects and advantages are realized and although a preferred embodiment has been disclosed and described in detail herein, its scope should not be limited thereby, rather its scope should be determined by that of the appended claims.

What is claimed is:

1. In a device for performing acoustical imaging of portions of the internal morphology of the respiratory tract, which includes an extended hollow acoustic pipe having a speaker at one end and being open at its opposite end and at least one first microphone located on the pipe's wall, the improvement comprising:

a thin-wall tube being hollow and open on one end, the tube includes a first filter therein for protecting the speaker from humidity and a second filter co-extensive with the first microphone, said tube being so dimensioned so as to fit snugly in the acoustic pipe; and said tube being coextensive with the acoustic pipe whilst not affecting the acoustic testing done by the device.

2. The invention in accordance with claim 1 wherein the tube includes an opening for positioning with respect to the first microphone with said second filter being positioned over said opening.

3. The invention in accordance with claim 1, which includes a second microphone, wherein said first and second microphones are located on the pipe's wall and the tube includes two respective openings for the first and second microphones with filters positioned over said openings.

4. The invention in accordance with claim 3 which includes sealing means at the tubes open end for creating a seal between the tube and the acoustic pipe.

5. The invention in accordance with claim 4 wherein said sealing means is an O-ring.

6. The invention in accordance with claim 4 wherein said sealing means is a flexible lip.

7. The invention in accordance with claim 3 which includes alignment means for properly aligning the tube in the pipe.

8. The invention in accordance with claim 7 wherein said means comprises a slot in the tube which engages with a port positioned on the pipe's wall.

9. The invention in accordance with claim 1 which includes alignment means for properly aligning the tube in the pipe.

10. The invention in accordance with claim 9 wherein said means comprises a slot in the tube which engages with a port positioned on the pipe's wall.

11. The invention in accordance with claim 10 wherein the tube is disposable and is made of a plastic material.

12. The invention in accordance with claim 1 which includes sealing means at the tubes open end for creating a seal between the tube and the acoustic pipe.

13. The invention in accordance with claim 12 wherein said sealing means is an O-ring.

14. The invention in accordance with claim 12 wherein said sealing means is a flexible lip.

* * * * *